(12) United States Patent  (10) Patent No.: US 8,394,322 B2
Windeyer et al.  (45) Date of Patent: Mar. 12, 2013

(54) HISTOLOGICAL TISSUE SPECIMEN TREATMENT

(75) Inventors: Victor Camfield Windeyer, South Yarra (AU); Michael Houston Drummond, Glen Waverly (AU); Stephen Gregory Phillip, Hawthon (AU)

(73) Assignee: Leica Biosystems Melbourne Pty Ltd, Victoria (AU)

( * ) Notice: Subject to any disclaimer, the term of this patent is extended or adjusted under 35 U.S.C. 154(b) by 560 days.

(21) Appl. No.: 12/062,324

(22) Filed: Apr. 3, 2008

(65) Prior Publication Data

US 2008/0220468 A1  Sep. 11, 2008

Related U.S. Application Data

(62) Division of application No. 10/491,290, filed as application No. PCT/AU02/01337 on Oct. 1, 2002, now Pat. No. 7,371,346.

(30) Foreign Application Priority Data

Oct. 1, 2001  (AU) .............................................. 8021
Sep. 27, 2002 (AU) ............................... 2002952417
Oct. 1, 2002  (AU) .............................................. 8023

(51) Int. Cl.
  *G01N 21/00*  (2006.01)
(52) U.S. Cl. ................. 422/63; 422/64; 422/65; 422/66; 422/67; 422/536; 436/180
(58) Field of Classification Search ............... 422/63–67, 422/99–100, 500–502, 536; 436/180
See application file for complete search history.

(56) References Cited

U.S. PATENT DOCUMENTS

| 3,301,318 | A |   | 1/1967  | Haske |
|---|---|---|---|---|
| 3,889,014 | A |   | 6/1975  | Kinney et al. |
| 3,892,197 | A | * | 7/1975  | Kinney et al. ................. 118/667 |
| 4,141,312 | A |   | 2/1979  | Louder et al. |
| 4,483,270 | A | * | 11/1984 | Toya et al. .................... 118/694 |
| 4,729,876 | A | * | 3/1988  | Hennessy et al. ............. 422/539 |
| 4,911,915 | A |   | 3/1990  | Fredenburgh |
| 5,049,510 | A |   | 9/1991  | Repasi et al. |
| 5,084,133 | A |   | 1/1992  | Guy et al. |

(Continued)

FOREIGN PATENT DOCUMENTS

DE  199 52 349       6/2000
EP  0 753 745 A2    1/1997

(Continued)

OTHER PUBLICATIONS

Willis, Donna, "Microwave Tissue Processing," EBSciences Company, Nov. 1997, Retrieved Mar. 5, 2003, from www.ebsciences.com/staining/biopsy.htm, 3 pp.

(Continued)

*Primary Examiner* — Jyoti Nagpaul
(74) *Attorney, Agent, or Firm* — Sughrue Mion, PLLC

(57) ABSTRACT

A tissue processor for processing tissue samples for histological analysis. The processor comprises two retorts, wax baths, reagent containers, a pump and valve. The vale distributes the reagent from one container to either retort. Separate reagent lines connect the wax baths to the retorts. A method of infiltrating a sample containing a reagent such as a dehydrating reagent like an alcohol, where the infiltrating material is heated to a temperature at or above the boiling point of the reagent, to boil off the reagent when the tissue sample is contacted by the infiltrating material. The pressure in the retort may be reduced to lower the boiling point of the reagent.

8 Claims, 10 Drawing Sheets

U.S. PATENT DOCUMENTS

| | | | |
|---|---|---|---|
| 5,089,288 | A | 2/1992 | Berger |
| 5,158,895 | A | 10/1992 | Ashhara et al. |
| 5,282,149 | A | 1/1994 | Grandone et al. |
| 5,357,095 | A | 10/1994 | Weyrauch et al. |
| 5,437,838 | A | 8/1995 | DeMoranville et al. |
| 5,725,835 | A | 3/1998 | Lautenschlager |
| 5,839,091 | A | 11/1998 | Rhett et al. |
| 6,048,722 | A | 4/2000 | Farb et al. |
| 6,096,561 | A | 8/2000 | Tayi |
| 2001/0003652 | A1 | 6/2001 | Freeman |
| 2001/0029320 | A1 | 10/2001 | Trumbull et al. |
| 2001/0051365 | A1 | 12/2001 | Morales et al. |
| 2001/0055799 | A1 | 12/2001 | Baunoch et al. |
| 2002/0131896 | A1 | 9/2002 | Hunnell et al. |
| 2007/0243626 | A1 | 10/2007 | Windeyer et al. |

FOREIGN PATENT DOCUMENTS

| | | |
|---|---|---|
| GB | 2 334 688 | 9/1999 |
| JP | 63-144258 A | 6/1988 |
| JP | 3-68865 A | 8/1989 |
| JP | 03-068866 A | 3/1991 |
| JP | 11502926 | 3/1999 |
| JP | 11-271194 A | 10/1999 |
| JP | 11-513123 A | 11/1999 |
| JP | 2001516869 A | 10/2001 |
| JP | 2003517601 A | 5/2003 |
| JP | 2003522935 A | 7/2003 |
| JP | 2001194278 | 7/2007 |
| RU | 2 104 513 | 10/1998 |
| SU | 1317307 | 6/1987 |
| WO | WO 86/06479 | 11/1986 |
| WO | 9319207 | 9/1993 |
| WO | WO 98/25140 | 6/1998 |
| WO | 99/09390 A1 | 2/1999 |
| WO | 9909390 A1 | 2/1999 |
| WO | 0036393 | 6/2000 |
| WO | 0036393 A2 | 6/2000 |
| WO | WO 00/47975 | 8/2000 |
| WO | WO 01/31347 | 5/2001 |
| WO | 0144783 A1 | 6/2001 |
| WO | WO 01/44783 A1 | 6/2001 |
| WO | 03/029845 A2 | 4/2003 |

OTHER PUBLICATIONS

"Tissue Processing," Medical Library, Univ. of Utah, Histology, School of Medicine, Utah, Dec. 6, 1988. Retrieved Mar. 6, 2003, from www.medlib.med.utah.edu/WebPath/HISTHTML/HISTOTCH/HISTOTCH.html, 2 pp.

Sutton, R., "Simple Distillation Laboratory #1 Chemistry 220," Lab Notes, School of Chemistry, Kalamazoo Valley Community College, Michigan, Aug. 30, 2001. Retrieved Mar. 5, 2003, from http://puma.kvcc.edu/rsutton/C220/simple_distillation.htm, 2 pp.

"TPC 15 Tissue Processing Center," Medite Company site, catalog of products, first version published Feb. 21, 2001. Retrieved Mar. 5, 2003, from www.medite.de/englisch/geraeteprogramm/geraeteprogramm/tissue_processing_center.htm, 4 pp.

Supplementary European Search Report for Application No. EP 02 78 7194. Apr. 15, 2009.

Ultrarapid vacuum-microwave histoprocessing; Kok, et al; Histochemical Journal 27, 411-419 1995, pp. 2-10.

Japanese Office Action for Application No. 2010-284970; Jun. 26, 2012.

European Search Report dated May 7, 2012 issued in corresponding European patent application No. 11190008.0.

* cited by examiner

HISTOLOGICAL TISSUE SPECIMEN TREATMENT

PRIORITY

This application is a divisional of application Ser. No. 10/491,290, filed 17 Dec. 2004 now U.S. Pat. No. 7,371,346, which is a national stage application of international application PCT/AU02/01337, with an international filing date of 1 Oct. 1, 2002. Also, this application claims foreign priority from: PR 8021, AU, 1 Oct. 2001; PR 8023, AU, 1 Oct. 2001; and 2002952417, AU, 27 Sep. 2002.

FIELD OF THE INVENTION

This invention relates to systems and methods for the processing of histological tissue specimens.

BACKGROUND OF THE INVENTION

Histological tissue specimen preparation is a physical process that involves chemical solutions reacting with biological specimens. Typically specimens such as tissue samples from biopsies and autopsies require processing. The end result of such processing is a sample that has been preserved, and been infiltrated with paraffin. Once the tissue has been embedded in the paraffin, it is stable and may then be subsequently embedded and then sectioned on a microtome. This process has typically involved four different sub-procedures.

(a) Fixation.

Fixation is a process by means of which cell proteins are stabilized, and the process is normally performed using chemical solutions. A good fixative is usually a fluid that will neither shrink nor swell the tissue, and more particularly will not dissolve its constituent parts, but will kill bacteria and render enzymes inactive. In addition, the solution should modify tissue constituents in such a way that they retain their form when subjected to treatment that would have damaged them in their initial state. The most commonly used chemical solution is formalin.

(b) Dehydration

Since the ultimate purpose of tissue specimen treatment is to infiltrate the tissue sample in paraffin, and since water and paraffin are not miscible, the sample must be dehydrated after the fixation step. This is usually achieved by subjecting the tissue sample to increasing concentrations of alcohols.

(c) Clearing

After dehydration, the tissue sample is still not capable of accepting paraffin since paraffin and alcohol are not miscible. A chemical solution, selected to be miscible with both alcohol and paraffin, is used to clear the alcohol from the sample. The chemical solution most commonly used is xylene. Unfortunately, xylene is considered to be toxic although most histological processing laboratories use xylene on a daily basis.

(d) Infiltration

The fourth and final step in the tissue sample treatment is infiltrating the sample, usually with paraffin wax. In this step the cleared tissue samples are placed into paraffin heated to a few degrees above its melting temperature. Several changes of paraffin may be required to remove the residual xylene so that the tissue is completely infiltrated with the molten paraffin.

The timing of the fluid change for all the fluids relates to the requirement to effectively displace the previous chemical from the tissue samples. Tissue samples can vary considerably in content and size, and therefore there may be a large variation in the time required to displace the fluid from one sample compared to the time taken to displace fluid from another. Further, some samples are sandwiched between biopsy pads that are porous and absorb significant quantities of fluid.

The first attempt at automation of the previously manual method of tissue processing involved placing solutions in a circular arrangement so that samples could be moved from container to container until they reached the last heated paraffin reservoir. The most well known instrument with this type of configuration used in the histology field was the Technicon. One of the major disadvantages of instruments of this type was that they allowed fumes to escape into the laboratory, thus exposing the laboratory workers to a hazardous environment. To overcome this problem, the next generation of tissue processing instruments included a centrally located closed chamber for the tissue samples. The solutions necessary for tissue processing were delivered into the closed chamber using suitable valving where the fluids are pumped in and out of the chamber in sequence. Normally the chamber would not be opened during the process.

As the chamber is closed, and only a single protocol can be run, the protocol must attempt to cater for the range of tissue samples that may be included in a single run. This can result in either over processing or under processing of some samples. Given the sealed nature of the retort, tissue samples may not easily be removed or added during a processing run.

Another problem is that some samples require urgent processing, while other samples are not urgent. In the known tissue sample preparation apparatus it has not been possible to stop a current sample run to process a sample required urgently, or to employ a protocol that allows an urgently required sample to be processed with other samples that require longer processing times. Thus, either the urgently required sample is run in isolation, or it is put with other samples, increasing the processing time.

Examples of known automated tissue processing machines will be found in the patent literature, and typical examples include U.S. Pat. No. 4,141,312 Louder, and U.S. Pat. No. 5,049,510 Repasi et al.

The prior art has therefore been unable to deal adequately with ensuring that a variety of samples can be processed safely and efficiently.

Some systems include heating of wax or tissue samples with microwaves, however microwave systems are difficult to automate, and preferentially heat the tissue sample rather than the reagents.

There is a need in the art for a tissue processor that provides automation to tissue processing.

There is also a need to reduce the use of hazardous chemicals employed in tissue processing.

There is a further need to clear infiltrating material of contaminants.

SUMMARY OF THE INVENTION

In one form, the present invention relates to a tissue processor having two retorts, a controller and a set of reagent containers fluidly connected to the retorts by reagent conduits and a valving arrangement, wherein the valving arrangement directs reagent from the reagent containers into either of the retorts, as directed by the controller.

In another form the present invention relates to a method of processing a tissue sample including the steps of:

dehydrating fixed tissue by exposing a tissue sample to a dehydrating solution;

infiltrating the dehydrated tissue samples by exposing the tissue to an infiltrating material;

wherein the step of removing the dehydrating fluid is accomplished by heating the infiltrating material to a temperature substantially equal to, or above the boiling temperature of the dehydrating solution, and contacting the tissue sample with the infiltrating material so that dehydrating solution on the sample boils enabling the infiltrating material to infiltrate the tissue sample.

In a another form the present invention relates to a method of cleaning tissue processor infiltrating material of volatile contaminants including the steps of:

heating the infiltrating material to a cleaning temperature; and subjecting the infiltrating material to reduced pressure to lower the boiling point of the volatile contaminants wherein the cleaning temperature is substantially equal to or above the boiling temperature of the contaminants at said reduced pressure.

Embodiments of tissue processors of the present invention are described in greater detail below with reference to the accompanying diagrams.

DESCRIPTION OF PREFERRED EMBODIMENT

Figure 1:
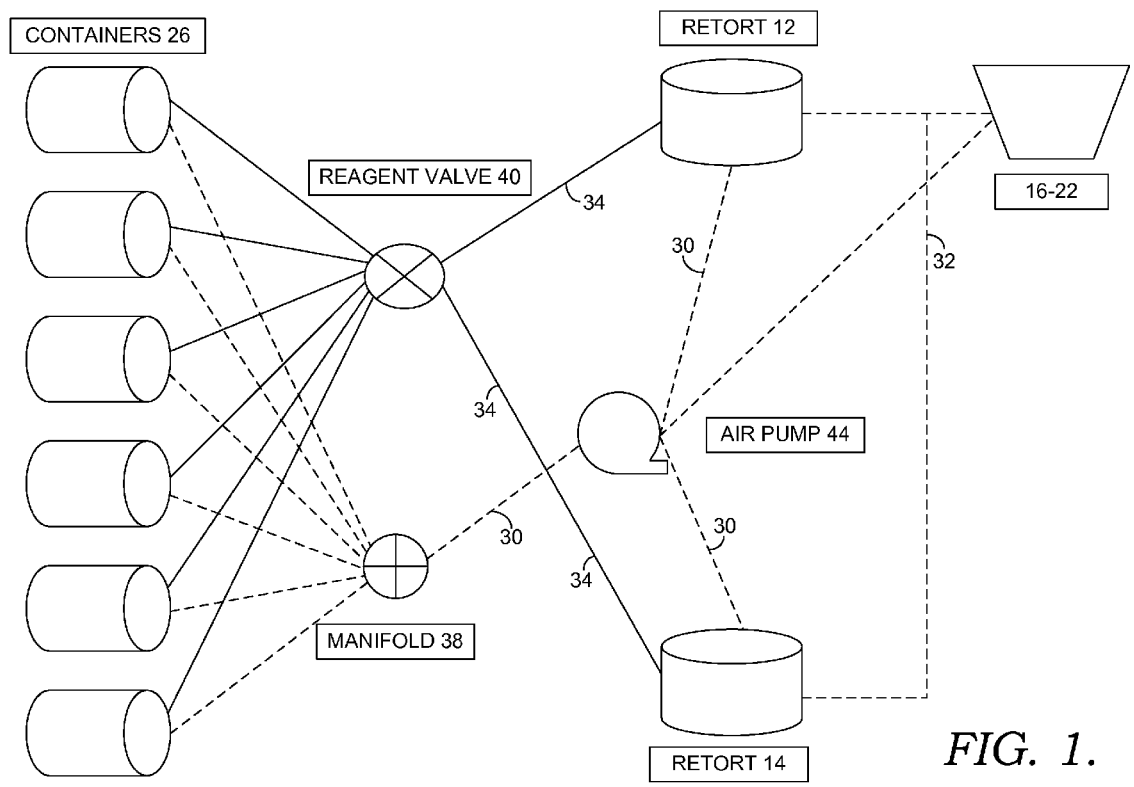
FIG. 1 is a simplified schematic block diagram of a first embodiment of a tissue processor according to the invention showing the basic elements of a tissue processor.
Figure 2:
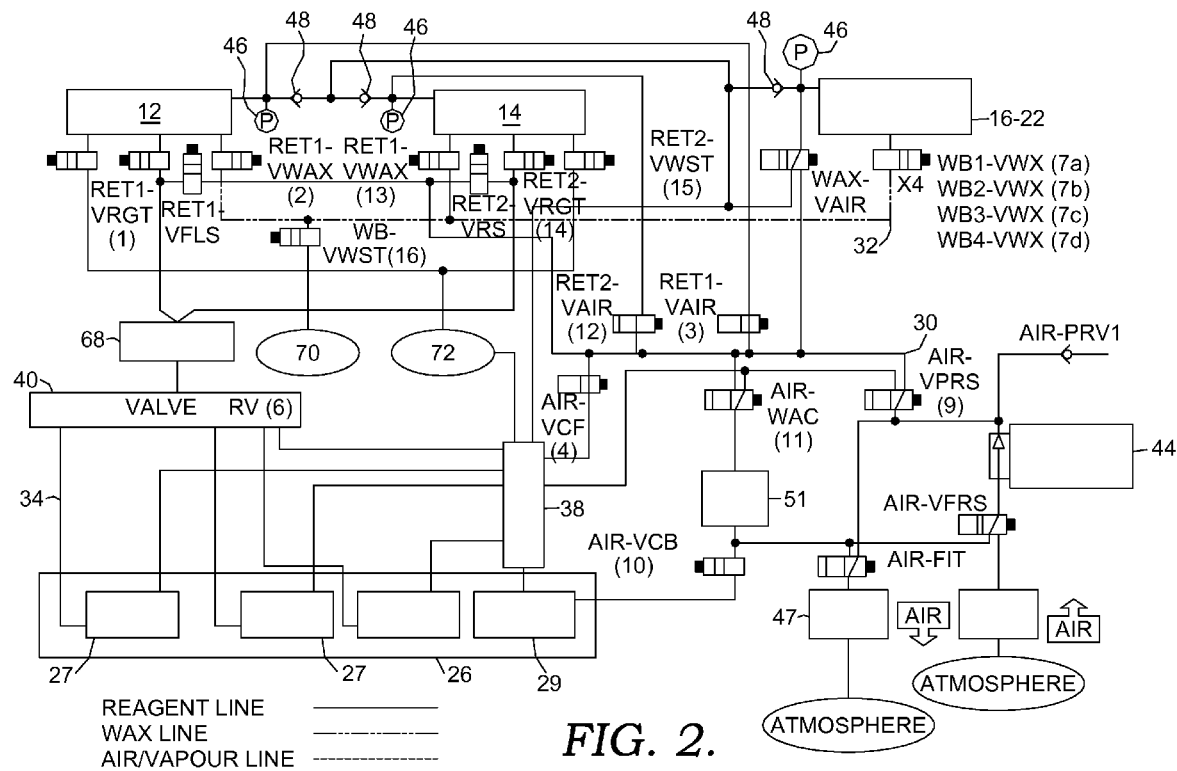
FIG. 2 is a more comprehensive schematic block diagram of a tissue processor showing air and reagent lines.

In FIG. 1 an example of a general schematic of the processor 10 is shown, indicating major features such as retorts 12 and 14, four infiltrating baths 16-22, containers 26, reagent valve 40, manifold 38, and air pump 44. There are three main fluid sub-systems connecting the major elements, one sub-system being the air lines 30 from pump 44 to infiltrating baths 16-22 and retorts 12 and 14. A second sub-system being infiltrating lines 32 connects infiltrating baths 16-22 to the retorts 16-22. A third sub-system is reagent lines 34 connecting the containers 26 to the reagent valve 40 and the retorts 12 and 14. Valving as shown in FIG. 2 ensures that fluid flows along the lines to the correct destination, and FIG. 2 shows a specific embodiment of fluid line connection and valve placement relative to the aforementioned elements. The electrical connections between the controller 25, valves, pump 44 and other elements have been omitted from FIG. 2 for clarity, and are considered standard fittings. Also omitted from FIG. 2 is the numerous containers 26 and their respective connections to the reagent valve 40, to provide clarify. The omitted connections are identical to the connections shown in FIG. 2.

Figure 3:
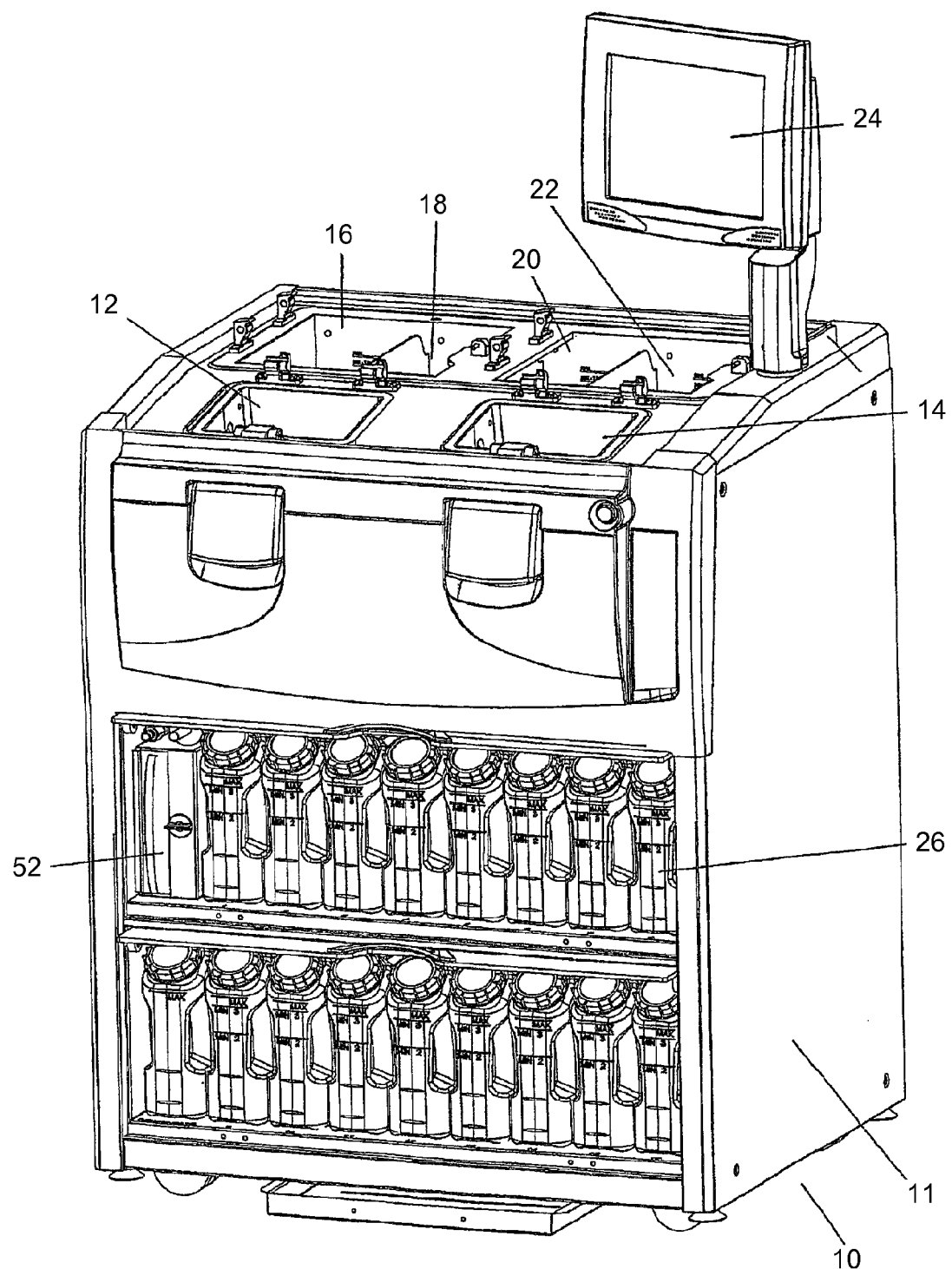
FIG. 3 shows a perspective view of an embodiment of the tissue processor shown in FIG. 2.
Figure 9:
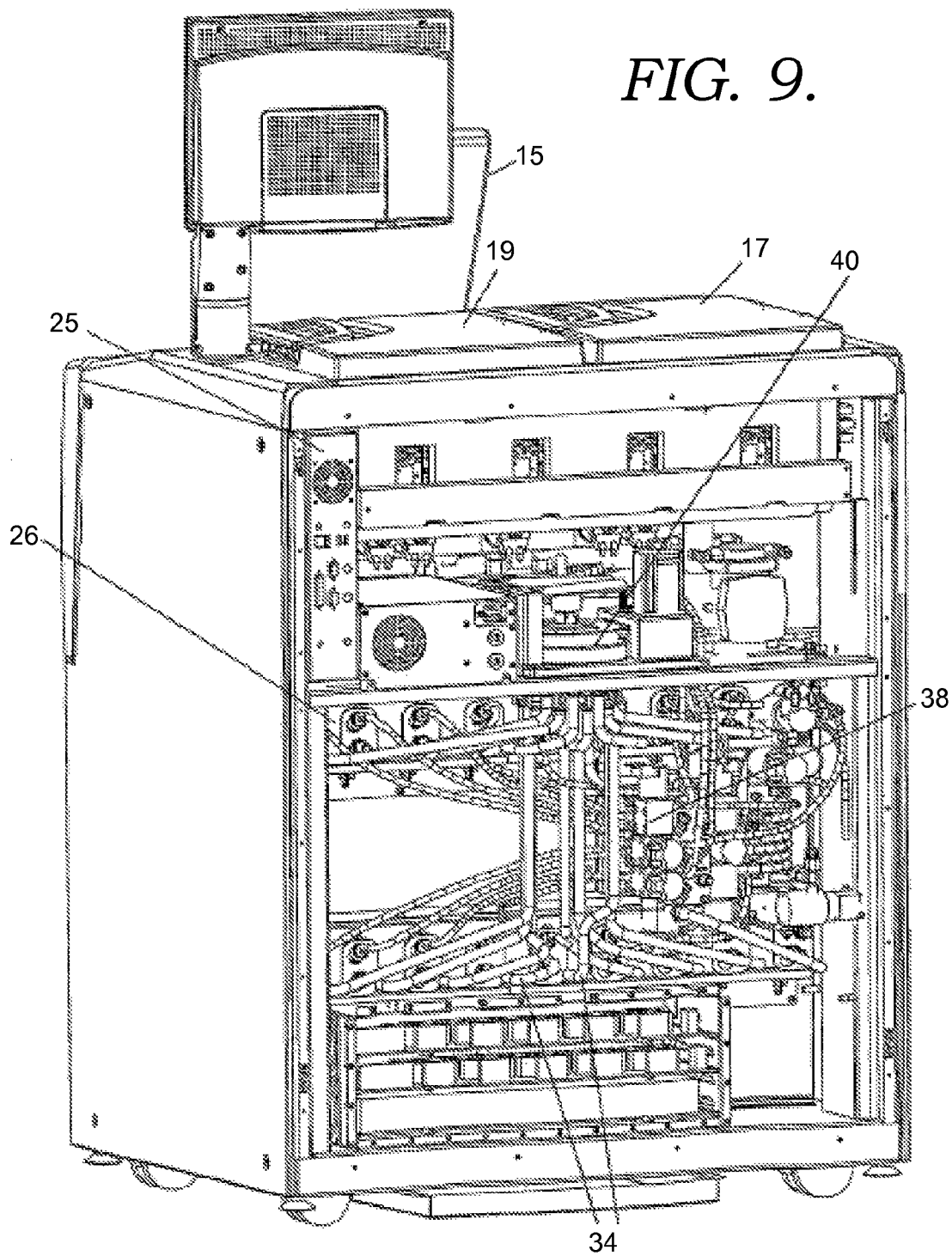
FIG. 9 shows a rear view of the tissue processor shown in FIG. 3.

The schematic of FIG. 2 is embodied in the examples shown in FIGS. 3 and 9.

With reference to FIGS. 3 and 9, the processor 10 includes control interface 24 that employs a graphical user interface to enable a user to operate the processor by controller 25. In the present embodiment the controller 25 is located in cabinet 11, however the interface 24 and controller 25 may be located separately, for example as part of a stand-alone personal computer. The controller 25 may include a personal computer processor such as a Celeron chip by Intel Corporation located on an ETX form factor PCB (not shown). The controller may contain a number of predefined protocols (or steps) for processing tissue, the protocols being stored in a non-volatile memory such as a hard drive. Protocols may be programmable by the user to implement a number of steps for tissue processing, or predefined. Typical protocol parameters include which reagents are to be applied to the samples, how long the reagents are to be applied, the temperature at which the reagents are applied, whether agitation is to take place, and whether ambient pressure in the retort is to be changed.

In FIG. 3, the retort 12 and 14 can be seen in front of infiltrating baths 16-22. The lids for the retorts 12 and 14 have been removed for clarify, as have the lids for the infiltrating baths. In the present embodiment each retort 12 and 14 would have a lid (not shown), and each pair of infiltrating baths would also have a lid 17 and 19 (shown in FIG. 9). The lids may seal with the retorts and baths when in a closed position. The containers 26 may be located under the retorts 12 and 14 so as to be accessible to a user. The controller interface 24 in FIGS. 3 and 9 employs a touch screen, however other input and display devices may be employed. Also located under the retorts 12 and 14 is a filter unit 52, which typically includes a carbon filter to absorb vapours from air expelled from the processor 10.

In FIG. 9 the various fluid lines such as reagent lines 34 from reagent containers 26 can be seen attached to a reagent valve 40. The reagent valve 40 may have inputs form all containers 27, and a single output to retorts 12 and 14. A number of air lines can also be seen connecting manifold 38 to the reagent bottles 26. The connections between various elements in FIG. 9 are shown schematically in FIG. 2.

Figure 4:
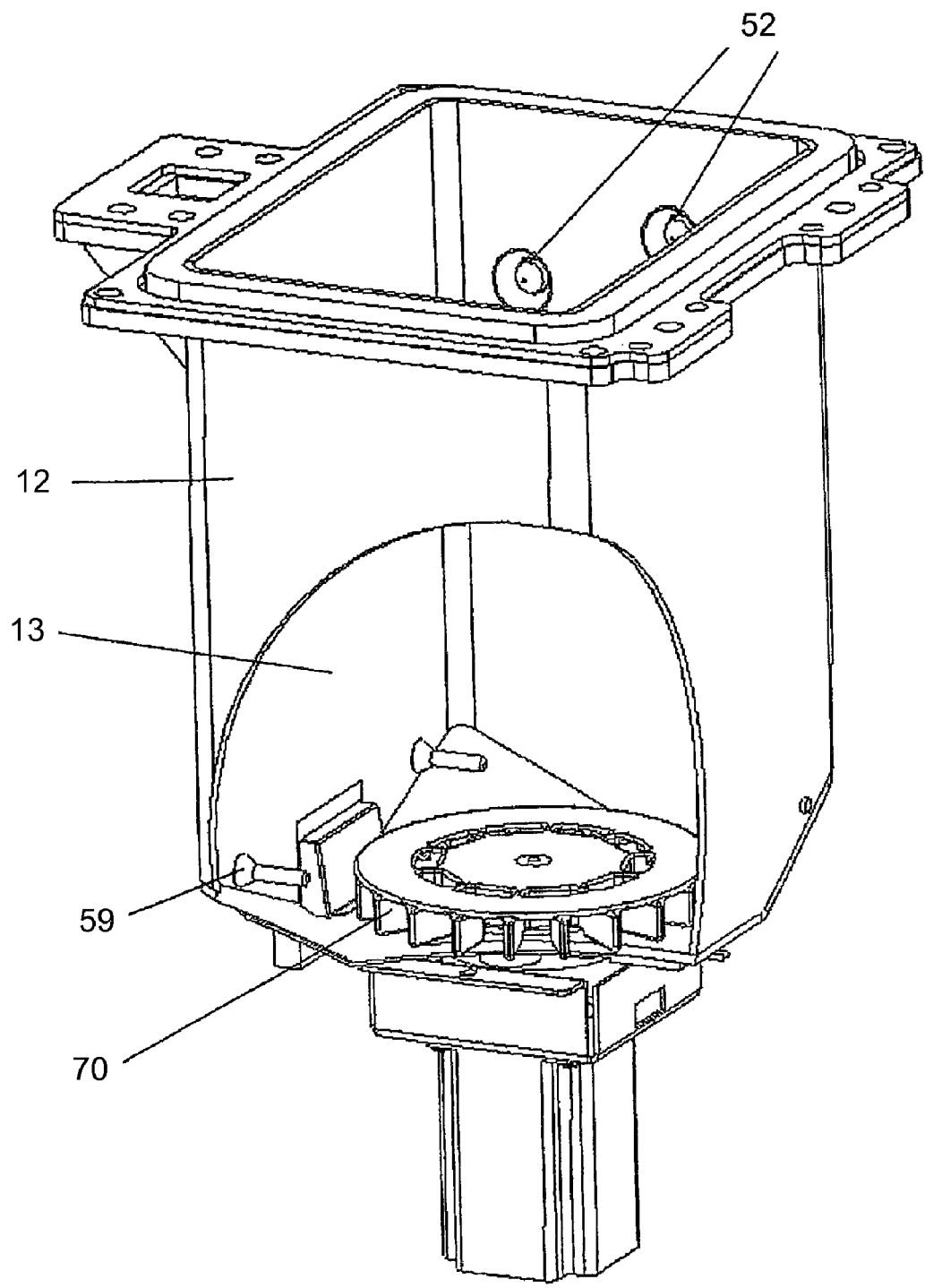
FIG. 4 shows a perspective cut-away view of a retort of the tissue processor shown in FIG. 3.
Figure 5:
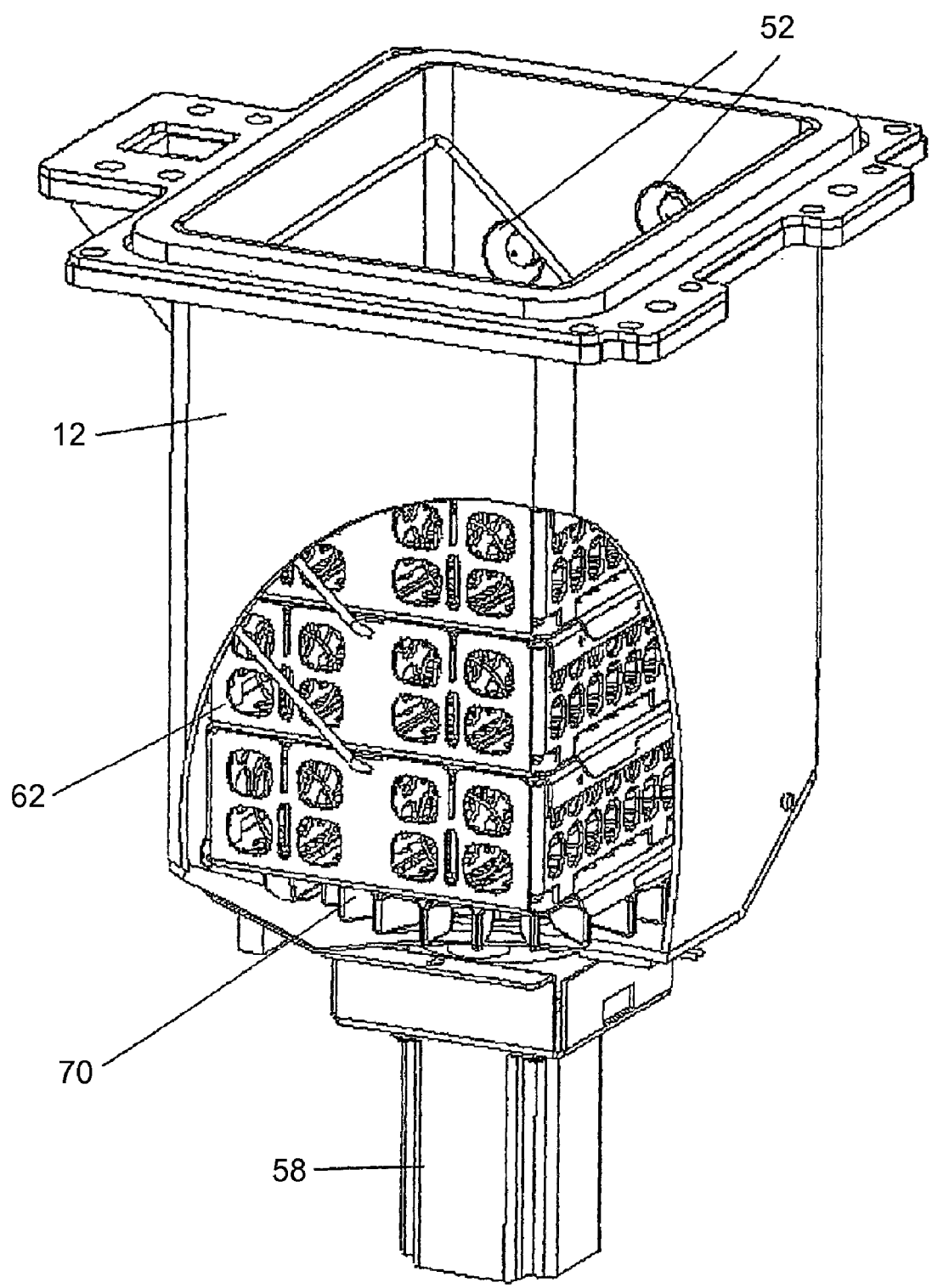
FIG. 5 shows a similar perspective cut-away view of the retort of FIG. 4 with cassette baskets in place.
Figure 6:
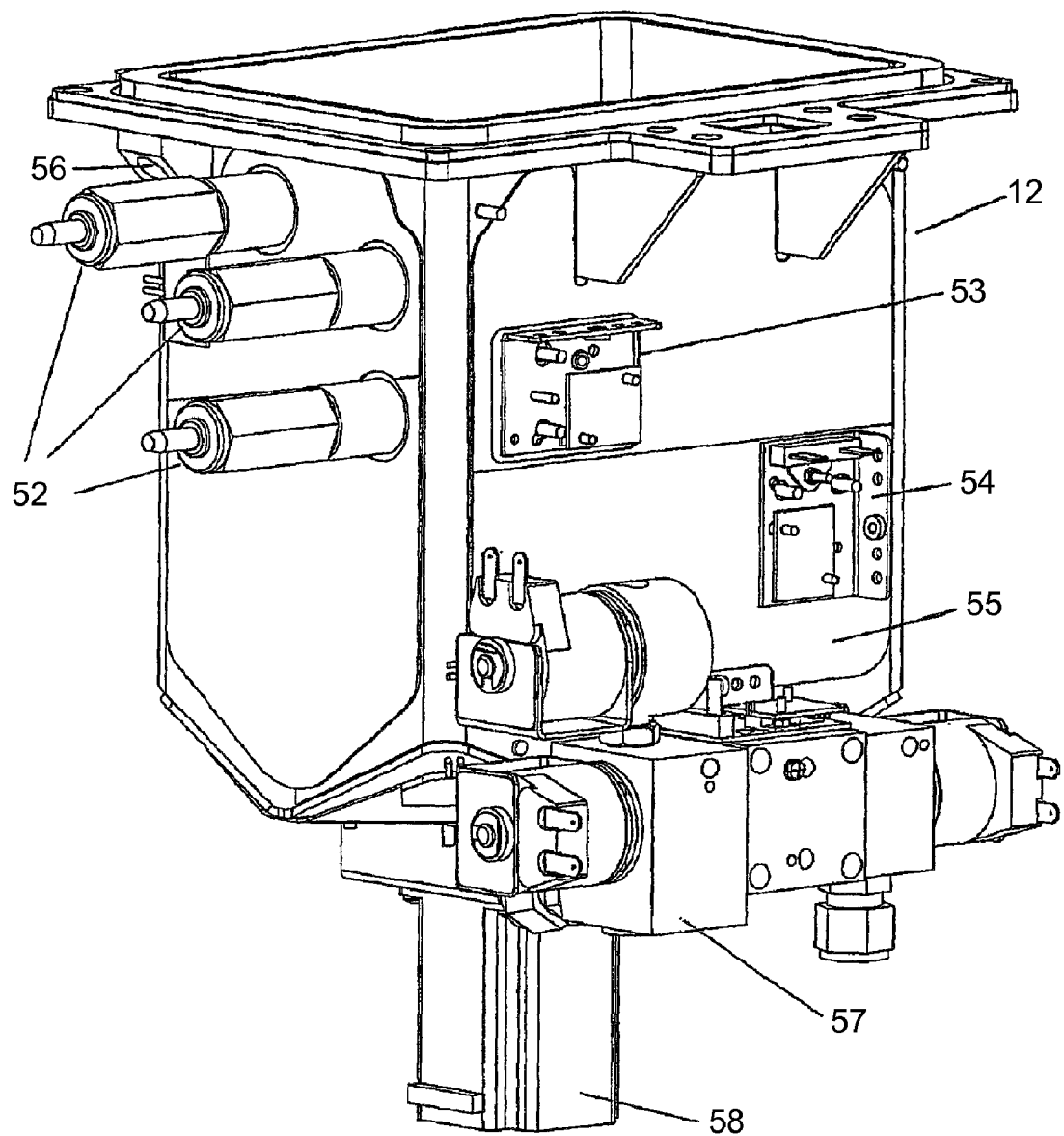
FIG. 6 shows a front view of the retort shown in FIG. 4.

One embodiment of retort 12 is shown in FIGS. 4-6, including a receptacle 13 for receiving baskets 62 containing tissue samples. The receptacle has a working capacity of 5.5 litres, however it may not necessarily be completely filled during each step of a protocol. When located in the processor, the retort may be rotated 10 degrees forward towards the front of the processor 10. This allows easier access to the baskets, as well as providing a drainage point which is lowermost in the receptacle 13, minimizing residuals remaining in the retort 12 after draining.

Sensors 52 are used to detect the level of fluid within the retort 12, so that the controller 25 can ascertain when to turn the pump 44 on or off, or open and close the appropriate valves, as described below. In FIG. 6, the placement of the three sensors 52 can be seen. The lowermost sensor detects when the level of liquid, for example reagent or infiltrating fluid, is above a minimum level. The minimum level may represent a partially filled receptacle which is desirable when operating in economy mode. This is desirable when two or less baskets are to be processed at once, whereupon only approximately 3.8 litres of fluid are required to cover the baskets and samples contained therein. As the baskets may be various sizes, the level of the lowermost sensor and therefore fill volume for economy mode can vary in different embodiments of the retort 12. The middle sensor 52 detects when the level of liquid typically covers three baskets, which is a normal full load. The top sensor 52 detects an overfill situation. In this particular embodiment the sensors are optically based relying on a change in refractive index when liquid comes into contact with a prism (not shown) of the sensor. Each basket may hold approximately 100 samples either in individual cassettes or placed directly into the basket. Thus a full load for the embodiment of the retort 12 shown in FIGS. 4-6 is approximately 300 samples. The retorts may be made larger or smaller depending in requirements.

Also shown in FIG. 6 is temperature sensor 53 which is mounted directly to the retort 12, and temperature sensor 54 which is mounted to a heating mat 55. The retort 12 is heated to ensure correct reagent, or infiltrating fluid temperature. Placing a temperature sensor directly on the retort 12 allows the fluid temperature within to be measured more accurately than by measuring the temperature of the heating mat, especially where the fluid used may have low thermal conductivity. The temperature of the heating mat may then be kept at a maximum while the temperature of the retort 12 is below the maximum, providing more rapid heating than if only one temperature sensor was employed.

Port 56 shown in FIG. 6 allows connection of an air line 30 to the retort 12. Retort manifold 57 also allows connection of infiltrating line 30 and reagent line 34 through a common entry point (not shown) at the bottom of the receptacle 13. In FIG. 2, retort manifold 57 incorporates valves ret1-vrgt and ret1-vwax, and is located at the front of the processor 10 so that the lean angle of 10 degrees of the retort causes all fluid to drain towards the common entry point.

In FIGS. 4 and 5, the interior of the receptacle 13 is shown, including agitator 70. Agitator 70 is magnetically coupled to an electric motor 58, and may be driven at a number of speeds dictated by controller 25. The baskets 62 each contain up to 100 tissue samples. The baskets 62 are supported clear of the agitator on posts 59 shown in FIG. 4.

In the present example, retort 12 and 14 are of identical construction, size and operation, however one retort may be larger or more volumous[sic] than the other. Connections to and from retort 12 are duplicated on retort 14.

In FIG. 2, pressure relief valves 48 are shown in fluid communication with air lines 30, retorts 12 and 14, and the infiltrating baths. Any overpressure in these lines will result in excess air being vented to waste through the manifold and filter 47.

A list of valve functions is as follows:

Valves ret1-vwst and ret2-vwst connects retorts 12 and 14 to waste container 72, when a waste cycle is required. Only one retort will be emptied at once and therefore these valves only open one at a time. In another embodiment, the valves ret1-vwst and ret2-vwst may be omitted, and waste container 72 may be directly connected to the reagent valve 40. To drain to waste a reagent, the reagent valve 40 connects to the reagent line 34 connected to the waste container 72, and the valve on the retort is opened to drain reagent directly to the waste container 72.

Valves ret1-vrgt and ret2-vrgt allow reagent flow into and out of their respective retorts during filling and draining of the retort. When draining a retort, these valves are open so that reagent may flow back down the reagent line and back into the same reagent container 26 from whence it came. It can be seen that air valves ret1-vfls and ret2vfls connect to the reagent lines 34 below the ret1vrgt and ret2-vrgt valves. These air valves are used to purge excess reagent from the reagent lines after filling one retort. This is desirable as using reduced pressure to draw fluid into a retort reduces fluid pressure along the whole reagent line 34, and therefore when pressure is restored to the reagent line 34 some reagent may travel up the line of the retort that was not filled. Opening these valves, or opening the valves and pumping air down the air lines into the reagent lines clears excess reagent, preventing or reducing cross contamination.

Valves ret1-vwax and ret2-vwax connect the retorts to the infiltrating baths, via infiltrating lines 32 and valves wb1-vwx to wb4-vwx. Valves ret1-vwax opens when infiltrating fluid is to enter or drain from retort 12, and wb1-vwx to wb4-vwx open one at a time depending on where the infiltrating fluid is being sourced. The infiltrating line 32 between the infiltrating baths and retorts is heated to ensure that the infiltrating material does not harden in the lines.

Valves ret1-vair and ret2-vair are used to control air from the air pump to the retorts. Air may be supplied either at a positive pressure to ambient, or withdrawn form the retorts so that pressure inside one or both retorts is below ambient pressure. These valves determine which retort is in fluid connection with the air pump. Also air-vprs must be open to allow communication between the pump and the valves, otherwise air is directed toward wax-air valve, connected to the infiltrating baths.

Figure 8A:
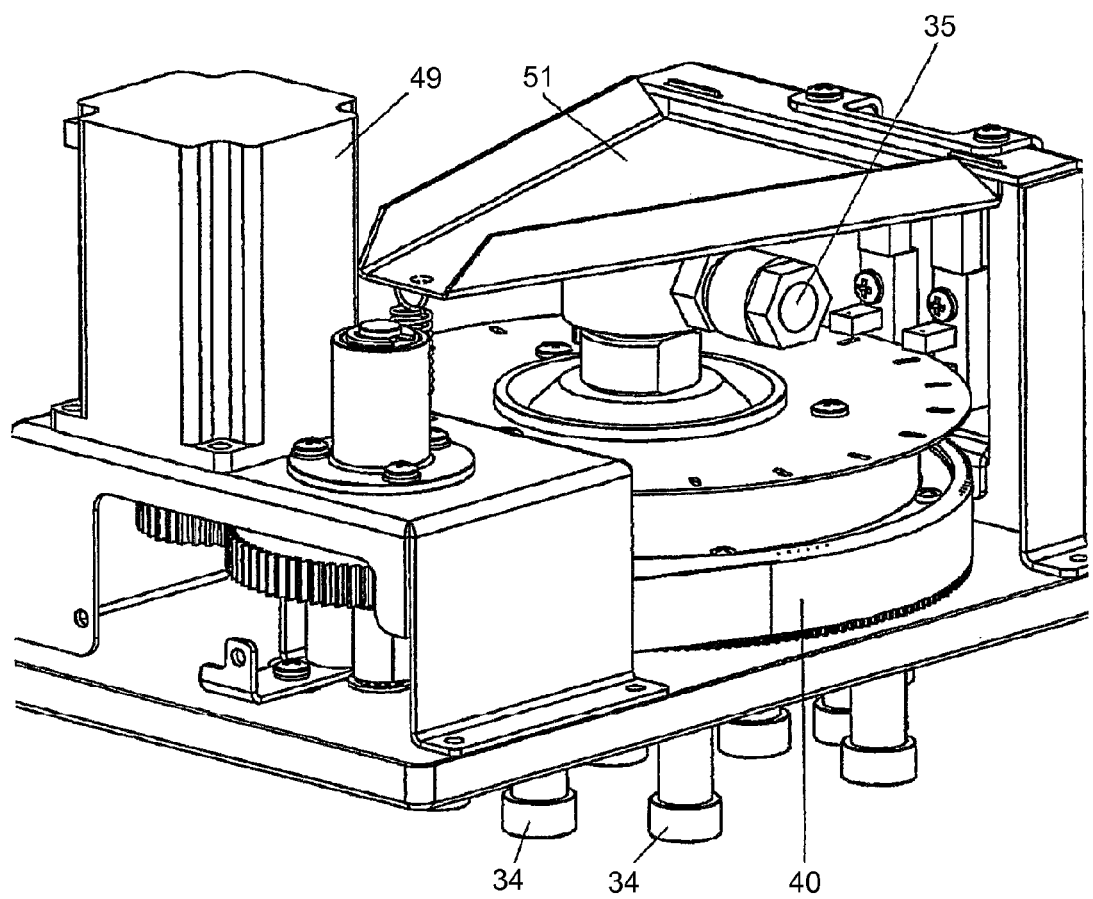
FIGS. 8a and 8b show views of an example of a reagent valve used in the tissue processor of the present invention.
Figure 8B:
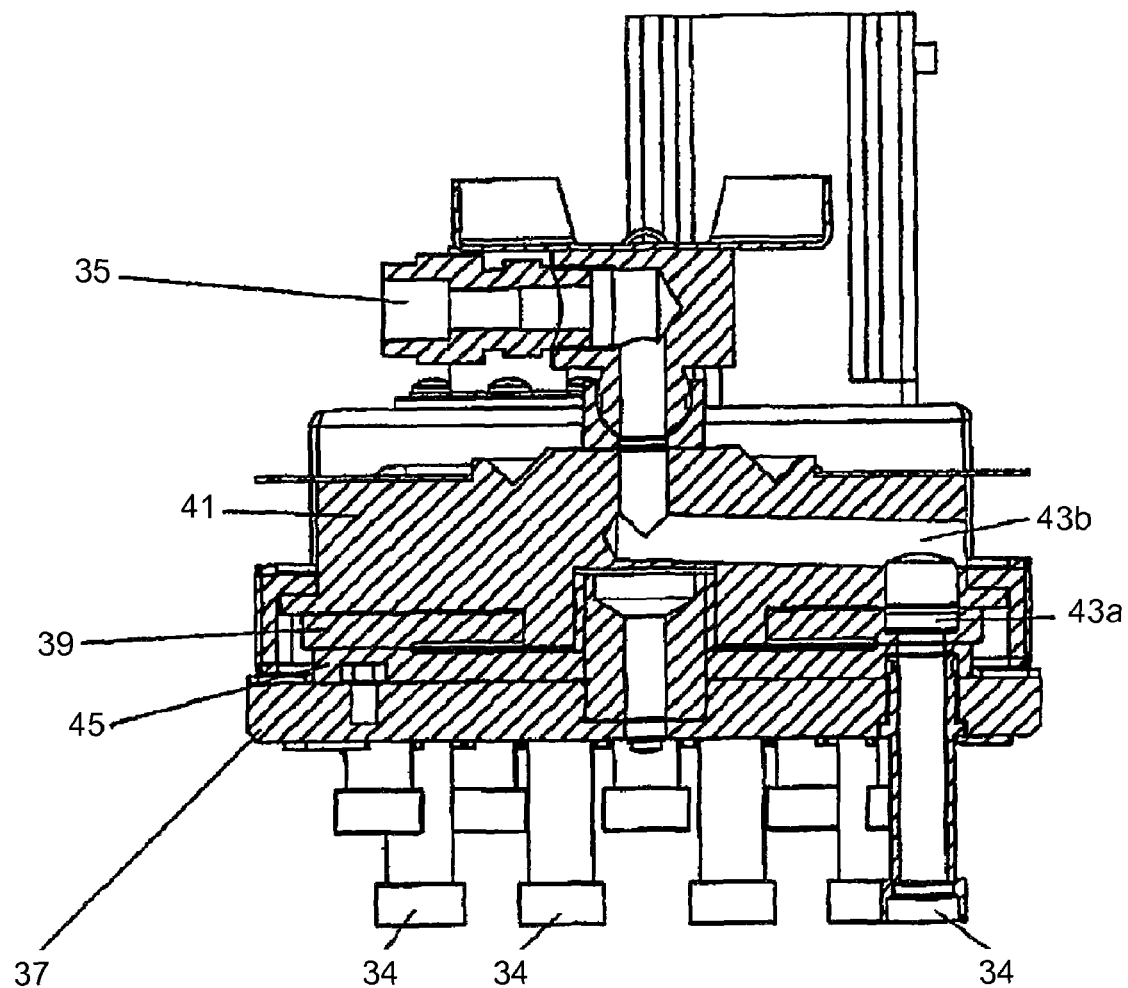

The reagent valve 40 is shown in FIGS. 8a and 8b, and includes connections between the reagent lines 34 from the reagent containers 26 on the input side, and outlet 35, which is fluidly connected to the retorts 12 and 14. The reagent valve 40 selects which reagent container will be in fluid communication with the reagent line connected to the retorts. In the present embodiment, the reagent lines 34 from the reagent containers 26 are arranged in a circle attached to the reagent valve housing 37. In the present embodiment, the reagent valve 40 is in the form of a rotary valve, having two ceramic discs 39 and 41, disc 39 having a single aperture 43a aligned with aperture 43b to form a conduit for reagent. The discs are mounted coaxially and adjacent each other and rotate together according to the position dictated by the controller 25. Disc 45 has an aperture for each reagent line 34, although in FIG. 8b only one aperture is in the place of the cross section. The rotating discs 39 and 41 rotate with respect to disc 45, driven by stepper motor 49 such that the apertures align to provide a flow path from the outlet 35 (and therefore one retort) to a reagent container 26. In order to assist with sealing between the discs 39, 41 and 45, a plate 51 applied pressure to the discs. In this way any reagent line 34 and therefore any reagent container can be selected by the controller 25 to be in fluid communication with one of the retorts 12 or 14. This type of valve has a small internal volume and therefore minimises cross contamination. Further, the reagents are drained back into the reagent containers after each step and therefore little reagent remains to contaminate the subsequent reagent. It should be noted that the infiltrating fluid does not pass through the reagent valve. This separation of fluid flows prevents the reagent valve from clogging and reduces the amount of cleaning of the valve.

In use, the tissue samples to be processed are typically placed into cassettes (not shown) for placement into a basket 62. Generally, tissue samples expected to have similar processing times and to be exposed to the same processing protocol are placed together in the same basket 62. The basket 62 containing the tissue samples is then placed into one of the retorts 12 or 14, and the lid closed, forming a sealed enclosure. An operator may then enter data into the control interface 24 to instruct the controller 25 of the protocol to be followed. The protocol may be programmed step by step, for example indicating the time, temperature, pressure, agitation and reagent for each step, or a pre-programmed protocol encompassing all steps may be selected.

The first step in a protocol, once the lid of the retort is secured, may be to fill the chosen retort (in this example retort 12 is chosen) with a fixing solution. A typical fixing solution is formalin, which may be held in one or more reagent containers. In order to fill the retort 12 with fixing solution, the pump 44 is switched on and valves open the air lines from the retort 12 to the inlet side of the pump, pumping air from the retort 12 chamber. The regent valve is set to a position that fluidly connects the reagent line of the retort 12 to the specified reagent container for formalin. Other valves are opened along the reagent lines from the retort 12 to the reagent valve 40. The reduced pressure in the retort 12 is sufficient to draw fluid out of the reagent container, through the reagent valve into the reagent lines 34 and into the retort 12. The retort is heated by heater pads to a predetermined temperature selected and controlled by the controller. Sensors 53 and 54 may be used to control the temperature of the retort, and therefore the tissue and any reagent contained therein. One or more sensors 52 in the retort as shown in FIGS. 4 and 6, may be used to detect the reagent level. When the reagent level in the retort is sufficient, typically to cover the baskets 62 as seen in FIG. 5, the pump may be turned off or otherwise disengaged from the retort 12, for example by closing valve ret1-vrgt shown in FIG. 2.

After a length of time determined by the controller 25 (typically as programmed by the user), the reagent may be removed from the retort 12. This is accomplished by opening valve ret1-vair in the air line 30 and opening valve ret1-vrgt in the reagent line 34. Reagent will then drain from the retort 12 back into the reagent container from which it came, or back into a different reagent container, or to waste, according to the position of the reagent valve 40 determined by the programmed protocol. To assist in draining, the retort 12 may be positively pressurised by air from the pump 44, supplied along the air lines 30. In the present embodiment the reagent drains back to its originating container. If the reagent is contaminated, or has been used for the predetermined number of samples or washes, then it is drained to waste using a separate waste cycle.

During the retort filling with reagent from a reagent container, the air pumped from the retort 12 flows down an air line 30, some of which flows back through manifold 38 and into the reagent container, recirculating some of the air from the retort 12. Excess air pumped from the retort 12 will flow out through a condensing mechanism such as a condensing coil 51, and/or a carbon filter 47, both of which are designed to remove volatile organic or other compounds from the air before it reaches the atmosphere. The processor 10 may have an outlet connection that allows the filtered air to be vented or further filtered by apparatus external to the processor 10.

The second step in tissue processing may be the dehydration step. The methodology employed to draw dehydrating reagent into the retort 12 may be the same as described above, as the dehydrating reagent will be stored in a reagent container 27. The dehydrating fluid may contain a fluid such as an alcohol, for example ethanol. The dehydrating fluid may also contain some water, either intentionally added, or, where the dehydrating fluid has been re-used, water removed from previous samples. There may be a number of steps of the protocol where dehydrating fluid is applied to the sample in the retort, and at each step a different dehydrating fluid may be used. For example, a fluid may be used that has less water than a previous fluid, to draw out more moisture from the sample at each wash. The dehydrating fluid may additionally or alternatively contain isopropanol. Later washes with isopropanol provide properties that may be advantageous, as will be described below. Further additives commonly used in tissue processor dehydrating fluids may be used, as the present embodiments are intended to be compatible with known dehydration fluids.

On a final wash with dehydrating fluid, the fluid is drained completely from the retort. This is accomplished by opening valves from the air pump as well as pumping air into the reagent lines to clear the reagent. A vapour flush may be employed where the pump flushes fresh air into the retort to clear any vapour from the reagent, such as a dehydrating fluid. Significant vapour may be present as the dehydrating fluid may have high partial pressure at the retort operating temperature. After the dehydrating step, a drying step may be employed, where the retort is heated by the heating mats 55, while air is pumped through the chamber by the air lines 30. This removes excess dehydrating fluid. The drying step may take several minutes or more, and the retort may be heated to 85 degrees Celsius, depending on the dehydrating fluid chosen and the sensitivity of the tissue samples to heat.

Another step in tissue processing is infiltrating of the samples. This is typically accomplished by an infiltrating material such as a paraffin wax. The wax is held in the infiltrating baths 16-22, which are heated to the desired temperature above the waxes melting temperature, which is typically 54 degrees Celsius. Wax pellets are typically added to an infiltrating bath, which heats the pellets until they melt and achieve a suitable temperature. Alternatively, pre-molten wax may be added directly to the baths. The wax is held at the elevated temperature, typically 65 degrees Celsius, until required. The present embodiment shows four infiltrating baths, however, there may be more or less depending on retort and infiltrating bath volume. The infiltrating lines 32 run from the infiltrating baths 16-22 to both retorts 12 and 14, and include valves such as ret1-vwax and ret2-vwax, that allow one, some, or all baths to be fluidly connected to one of the retorts. The arrangement of the baths, valves, and infiltrating material lines enables samples in one retort to be washed with up to four different infiltrating materials. Further, the infiltrating material can be heated in one or more baths while the processor 10 is in operation and drawing infiltrating material from the remainder of the baths.

Figure 7:
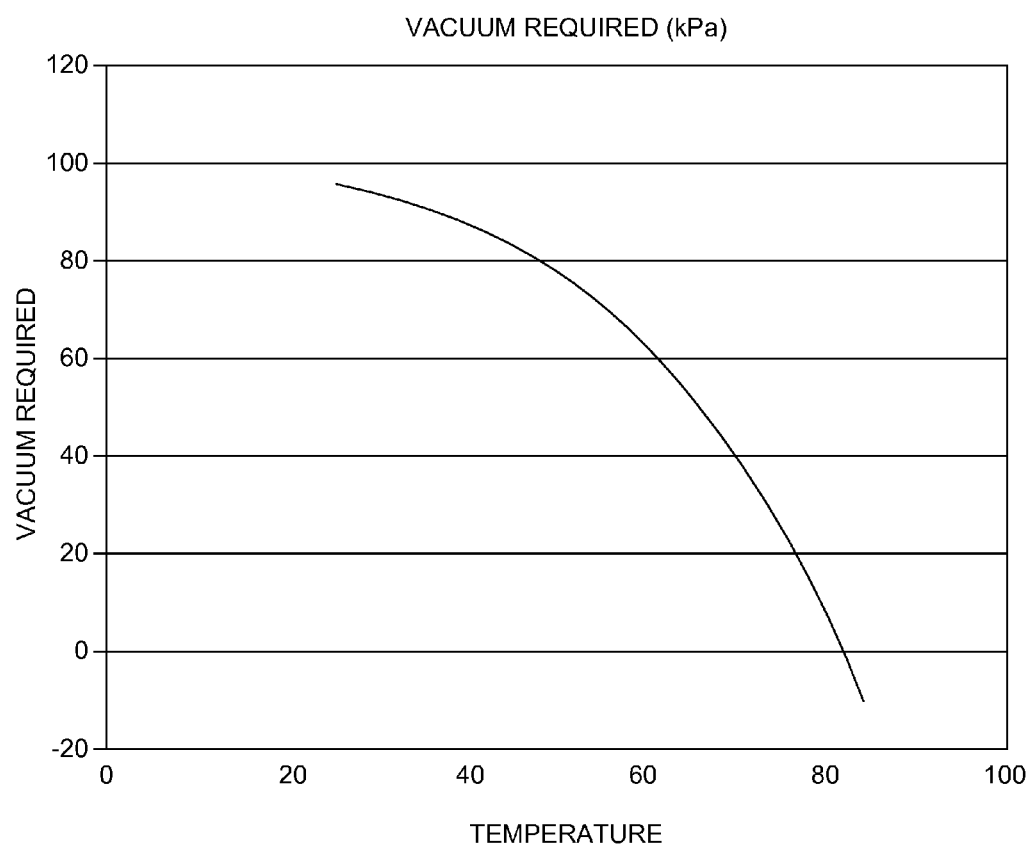
FIG. 7 shows a graph of isopropanol boiling temperature with respect to vacuum pressure.

During the infiltrating stage, the wax is drawn into the retort 12 by opening the valve between the retort and appropriate infiltrating bath, such as ret1-vfls, then reducing the pressure in the retort using the pump 44 and opening valves air-vprs and ret1-vair. The reduced pressure in the retort draws the wax into the retort 12. Typically the pressure may be −20 to −80 kpa gauge, however a wide variety of pressures may be used, and these are user programmable via the controller. The wax may be heated to a temperature above or approximately the same as the boiling temperature of the dehydrating fluid used in the last or last few washes. If an isopropanol is used, the boiling temperature will be approximately 82 degrees Celsius at atmospheric pressure. Ethanol typically boils at 78 degrees Celsius. After the retort has been drained of dehydrating fluid, some fluid remains on or absorbed by the tissue samples. The tissue samples may then be subjected to a drying stage as described above to remove further dehydrating fluid, and the retort flushed with clean air. Wax is then drawn into the retort. Upon contact with the heated wax, the remaining dehydrating fluid is evaporated or boiled off the tissue samples, and the wax replaces the dehydrating fluid, thus infiltrating the samples. The pump may continue to draw off air or vapour from the retort to reduce the pressure in the retort, which will reduce the evaporation temperature of the dehydration fluid. As an example, the pressure in the retort may be reduced by 50 kpa gauge, resulting in a boiling temperature of approximately 52 degrees Celsius for the isopropanol. A graph of boiling temperature compared to vacuum pressure is shown in FIG. 7. Reducing temperatures of the wax contacting the tissue samples may provide an advantage, for example where certain types of tissues do not perform well when exposed to high temperatures. Typically the paraffin wax used (Paraplast+from Oxford Laboratories) melts at about 54 degrees Celsius. Other infiltrating materials may be used including resins used in histological processes for infiltrating tissue samples. In the present example the alcohol used at the last stage, isopropanol, is not substantially miscible with paraffin wax. The means that infiltrating fluid is unlikely to penetrate the tissue sample if the previous fluid in the retort was immiscible with the infiltrating fluid. Boiling the volatile dehydrating material off therefore enables the omission of a step whereby an intermediary fluid such as xylene, which is miscible in alcohol and paraffin wax, is required: Xylene has undesirable properties in a laboratory. However, xylene will also evaporate when exposed to temperatures around 80 degrees, especially when the pressure inside the retort has been lowered by applying a vacuum as described herein. Thus the present example enables the tissue samples to be used without a xylene wash cycle, but also may be used with fluids such as xylene. There are advantages in not using xylene, including that xylene is miscible in wax, and therefore can be absorbed into the wax as a contaminant. However in some instances it is desirable to use xylene, for example when the tissue requires clearing and the dehydrating fluid such as isopropanol is deemed to be insufficient. Further, xylene may be used after a processing cycle to clean excess wax from the retort, and therefore xylene may be present in the processor.

It is possible to clean the infiltrating fluid of some of the volatile contaminants, such as the dehydrating fluid, clearing fluids such as xylene, by holding the wax in the bath and reducing the pressure in the bath. This clean cycle is done with the bath lid closed, whereupon the reduced pressure and holding the infiltrating material at an elevated temperature such as between 60 degrees and 100 degrees Celsius. In one embodiment the temperature may be held between 65 degrees and 85 degrees Celsius. By volatile material, it is meant that at the temperatures mentioned herein, and/or at reduced pressures, the material will boil or evaporate.

The vapour pressure of the dehydration fluid within the air in the container may also be reduced, for example by venting the air in the retort, either while maintaining a low pressure or cycling through pressure ranges. The infiltrating fluid may be held in the bath at an elevated temperature for several hours to clean away contaminants.

The use of two retorts allows two sets of baskets to be processed either simultaneously or with an overlap. Thus one retort can be loaded and a protocol begun while the other retort is mid-way through the same or a different protocol. This provides additional flexibility in the processor.

The tissue samples referred to in may be human or animal tissue samples, or samples from plant material.

An example protocol for tissue samples, such as a 3 mm punch human biopsy sample, will now be described:

| Step | Reagent | Time (min) | Temp (c.) | Retort Pressure | Agitation |
|---|---|---|---|---|---|
| 1 | Formalin | 5 | 60 | ambient | yes |
| 2 | 50/50 ethanol water | 25 | 60 | ambient | yes |
| 3 | 80/20 ethanol water | 35 | 60 | ambient | yes |
| 4 | Isopropanol | 30 | 60 | ambient | yes |
| 5 | Paraffin Wax | 40 | 85 | Vacuum | yes |
| 6 | Paraffin Wax | 5 | 85 | Vacuum | yes |
| | total time | 140 | | | |

Another protocol is as follows

| Step | Reagent | Time (min) | Temp (c.) | Retort Pressure | Agitation |
|---|---|---|---|---|---|
| 1 | formalin | 60 | 40 | ambient | yes |
| 2 | 80% ethanol | 45 | 40 | ambient | yes |
| 3 | 90% ethanol | 45 | 40 | ambient | yes |
| 4 | 100% ethanol | 60 | 40 | ambient | yes |
| 5 | 100% ethanol | 60 | 40 | ambient | yes |
| 6 | 100% ethanol | 60 | 40 | ambient | yes |
| 7 | 100% ethanol | 60 | 40 | ambient | yes |
| 8 | Isopar or d-limonene | 60 | 40 | ambient | yes |
| 9 | Isopar or d-limonene | 75 | 40 | ambient | yes |
| 10 | Isopar or d-limonene | 75 | 40 | ambient | yes |
| 11 | Paraplast | 70 | 60 | Vacuum | yes |
| 12 | Paraplast | 60 | 60 | Vacuum | yes |
| 12 | Paraplast | 60 | 60 | Vacuum | yes |
| | total processing time | 790 | | | |

From the above it can be seen that xylene is not required in this protocol, and that the protocol has few steps, saving time.

In one embodiment, a contamination detector 68 may be placed in the reagent line 34 to detect the presence of contaminants in the reagents.

To drain the retort 12, the pump may increase pressure in the retort 12 by pumping air along the same air lines 34 as used to draw reagent into the retort 12. Waste reagent may be drained into a reagent container, or be expelled to waste port 72. Infiltrating fluid may also be drained from the retort 12 to waste 70 by this method, and similarly infiltrating fluid may be drained from the baths using positive pressure.

In the above examples the dehydrating fluid is immiscible with the infiltrating material. However, the above process offers advantages even if a clearing cycle is used, where the clearing fluid is miscible with the dehydrating fluid and the infiltrating material. Further, additives may be used to increase the clearing properties of the dehydrating material, as well as increasing the miscibility of the fluids in the dehydrating and infiltrating steps.

While raising the temperature of the infiltrating fluid above the boiling temperature of the dehydrating reagent (or clearing reagent) will result in faster removal of the reagent, reagent will still be removed at or around the boiling temperature provided the partial pressure in the retort is lower than the partial pressure of the reagent at the given temperature. This can be accomplished by reducing the pressure in the retort, then allowing some fresh air into the retort. Bringing fresh air into the retort while removing air laden with vapour will reduce the partial pressure of reagent in the air in the retort thus promoting more evaporation of the reagent. If the reagent is miscible with the infiltrating fluid it may not be necessary to remove all the reagent to obtain infiltration. However, if the samples can withstand the temperature it is preferable to raise the temperature of the infiltrating fluid within the retort to a temperature above the boiling temperature of the reagent for the given pressure. A temperature about the boiling temperature of a reagent for a given pressure may be typically a few degrees, such as 5 degrees Celsius, of the boiling temperature.

Other dehydrating fluids are contemplated as being able to be used with the present apparatus, such as:
methanol
butanol
ethylene glycol
propylene glycol
industrial methylated spirits
Denatured alcohol (including alcohol denatured with kerosene, benzene or brucine)
Reagent grade alcohols
acetone
and combinations thereof,
however the above list is merely representative and is not intended to encompass an exhaustive list of reagents useful in the processor described herein.

Clearing reagents such as di-pentene, D-limonene, 1,1,1, trichloroethane, toluene, and dioxane are also contemplated, and again this list is meant to be indicative of the types of reagents that may be used, rather than an exhaustive list. The reagents above, and other reagents suitable for histological processes such as dehydrating, clearing or a combination thereof, may be used in the present apparatus with the step of evaporating the reagent from the sample using heating of the infiltrating fluid, provided the reagents evaporate without leaving a residue. While reagents such as butanol have a boiling point of approximately 118 degrees Celsius at atmospheric pressure, the boiling point drops dramatically with a reduction in ambient pressure. While it is believed preferable to not heat most tissues above 85 degrees Celsius, some types of well fixed tissue will survive this temperature without damage, and therefore higher temperatures may be used, increasing the range of reagents useful in the abovementioned processes. Accordingly, the upper temperature which may be used is dependent on the tissue, and therefore in well fixed tissue, temperatures may exceed 100 degrees Celsius. Reducing pressure in the retort will assist in reducing temperatures in the retort by reducing the boiling point of reagents.

Infiltrating materials such as resins and other fluids used in histological tissue processing are also contemplated in the above examples, and the present invention is not intended to be limited to the infiltrating materials mentioned herein. It is also contemplated that infiltrating material may be a mixture of substances, such as mineral oils and paraffin wax.

The invention claimed is:

1. A tissue processor having a set of reagent containers and infiltrating baths, and two retorts adapted to hold multiple tissue samples for processing, each retort connected to a valve, the reagent containers also connected to said valve, characterized in that the valve selectively connects one of the reagent containers to be fluidly connected to one of said retorts,
a plurality of infiltrating conduits which fluidly connect the infiltrating baths to the retorts and;
reagent conduits which fluidly connect the reagent containers with the retorts.

2. The tissue processor of claim 1 wherein a controller selects the position of the valve to fluidly connect one of the reagent containers to one of said retorts.

3. The tissue processor of claim 2 wherein the valve is a rotary valve.

4. The tissue processor of claim 3 wherein the valve has a plurality of ceramic plates that rotate with respect to each other to selectively connect a reagent container to one of said retorts.

5. The tissue processor of claim 1 wherein a pump provides positive or negative pressure in at least one of the retorts to draw or push reagent or infiltrating material into or from the respective retort.

6. The tissue processor of claim 1 having a first temperature sensor mounted directly to the body of a first retort of said retorts, and a second temperature sensor mounted to a heating mat of said first retort.

7. An apparatus for processing tissue having at least a retort, a number of reagent containers, at least one infiltrating material container, a reagent valve for directing reagent selectively from one of said reagent containers to a said retort, a heater, and a temperature sensor, a heating pad and a controller for heating the heating pad to heat the at least one retort to a temperature substantially equal to or above a reagent evaporation temperature to evaporate the reagent from said retort.

8. The apparatus of claim 7 including a pump for lowering the pressure in the retort and increasing the pressure within the retort so as to assist in clearing the contents of the retort.

* * * * *